(12) United States Patent
Nishio et al.

(10) Patent No.: US 11,046,935 B2
(45) Date of Patent: Jun. 29, 2021

(54) GLUCOSE DEHYDROGENASE

(71) Applicant: Amano Enzyme Inc., Nagoya (JP)

(72) Inventors: Kyoichi Nishio, Kakamigahara (JP);
Yuzo Kojima, Kakamigahara (JP);
Shotaro Yamaguchi, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 146 days.

(21) Appl. No.: 15/772,661

(22) PCT Filed: Oct. 26, 2016

(86) PCT No.: PCT/JP2016/081782
§ 371 (c)(1),
(2) Date: May 1, 2018

(87) PCT Pub. No.: WO2017/077924
PCT Pub. Date: May 11, 2017

(65) Prior Publication Data
US 2019/0153401 A1 May 23, 2019

(30) Foreign Application Priority Data

Nov. 6, 2015 (JP) .............................. JP2015-218852

(51) Int. Cl.
| | | |
|---|---|---|
| C12N 9/04 | (2006.01) | |
| C12N 1/15 | (2006.01) | |
| C12N 15/53 | (2006.01) | |
| C12Q 1/54 | (2006.01) | |
| C12M 1/34 | (2006.01) | |
| C12N 15/09 | (2006.01) | |
| G01N 33/66 | (2006.01) | |
| C12N 5/10 | (2006.01) | |
| C12Q 1/32 | (2006.01) | |

(52) U.S. Cl.
CPC ............. *C12N 9/0006* (2013.01); *C12M 1/34* (2013.01); *C12N 5/10* (2013.01); *C12N 15/09* (2013.01); *C12Q 1/32* (2013.01); *C12Q 1/54* (2013.01); *C12Y 101/9901* (2013.01); *G01N 33/66* (2013.01)

(58) Field of Classification Search
None
See application file for complete search history.

(56) References Cited

U.S. PATENT DOCUMENTS

| | | | |
|---|---|---|---|
| 2009/0176262 A1 | 7/2009 | Omura et al. | |
| 2009/0181408 A1 | 7/2009 | Tanaka et al. | |
| 2010/0192985 A1* | 8/2010 | Aehle | C11D 3/386 134/26 |
| 2015/0111280 A1 | 4/2015 | Sumida et al. | |
| 2016/0265021 A1 | 9/2016 | Aiba et al. | |

FOREIGN PATENT DOCUMENTS

| | | |
|---|---|---|
| EP | 2348108 A1 | 7/2011 |
| JP | 2000-350588 A | 12/2000 |
| JP | 2001-197888 A | 7/2001 |
| JP | 2001-346587 A | 12/2001 |
| WO | 2004/058958 A1 | 7/2004 |
| WO | 2007/139013 A1 | 12/2007 |
| WO | 2014/002973 A1 | 1/2014 |
| WO | 2015/060150 A1 | 4/2015 |

OTHER PUBLICATIONS

Nawa et al., J. Human Genet. 43:262-267, 1998 (Year: 1998).*
Yufeng Yang et al: "Efficient Expression, Purification, and Characterization of a Novel FAD-Dependent Glucose Dehydrogenase from Aspergillus terreus in Pichia pastoris", Journal of Microbiology and Biotechnology, vol. 24, No. 11, Nov. 28, 2014, pp. 1516-1524. (cited in the Apr. 16, 2019 Search Report issued for EP16861986.4).
Ryoko Satake et al: "Novel glucose dehydrogenase from Mucor prainii: Purification, characterization, molecular cloning and gene expression in Aspergillus sojae", Journal of Bioscience and Bioengineering, vol. 120, No. 5, Apr. 23, 2015, pp. 498-503. (cited in the Apr. 16, 2019 Search Report issued for EP16861986.4).
R. Satake: "Supplementary tables to Novel glucose dehydrogenase from Mucor prainii: Purification, characterization, molecular cloning and gene expression in Aspergillus sojae—Supplemental data", Journal of Bioscience and Bioengineering, Apr. 23, 2015, 9 pages. (cited in the Apr. 16, 2019 Search Report issued for EP16861986.4).
Anonymous: "NBRC 8869 Aspergillus iizukae Sugiyama", NBRC, 2004, 2 sheets. (cited in the Apr. 16, 2019 Search Report issued for EP16861986.4).
Search Report dated Apr. 16, 2019, issued for the European patent application No. 16861986.4.
T.G. Bak et al., "Studies on the Glucose Dehydrogenase of Aspergillus Oryzae," Biochim. Biophys. Acta, 139, 1967, pp. 265-276. (discussed in the spec).
T.G. Bak, "Studies on Glucose Dehydrogenase of Aspergillus Oryzae," Biochim. Biophys. Acta, 139, 1967, pp. 277-293. (discussed in the spec).
T.G. Bak et al, "Studies on Glucose Dehydrogenase of Aspergillus Oryzae," Biochim. Biophys. Acta, 146, 1967, pp. 328-335. (discussed in the spec).
Y Yang et al., "Expression, characterization and mutagenesis of an FAD-dependent glucose dehydrogenase from Aspergillus terreus," Enzyme Microb. Technol., 68, 2015, pp. 43-49. (cited in the ISR).
International Search Report dated Jan. 24, 2017, issued for PCT/JP2016/081782.

* cited by examiner

*Primary Examiner* — David Steadman
(74) *Attorney, Agent, or Firm* — Locke Lord LLP

(57) ABSTRACT

Intended is to provide a highly practical novel FAD-GDH. A glucose dehydrogenase having the following properties is provided: (1) action: catalyzes the reaction of oxidizing hydroxyl groups of glucose to form glucono-δ-lactone in the presence of an electron acceptor; (2) substrate specificity: reactivity to D-xylose is 10% or less when the reactivity to D-glucose is 100%; (3) pH stability: stable at pH 5 to 8; (4) amino acid sequence: including the amino acid sequence set forth in SEQ ID NO: 1, or an amino acid sequence with an identity of 83% or more to the amino acid sequence.

3 Claims, 9 Drawing Sheets

Specification includes a Sequence Listing.

| | Description | Max score | Total score | Query cover | E value | Ident | Accession |
|---|---|---|---|---|---|---|---|
| 1 | hypothetical protein ATEG_08295 [Aspergillus terreus NIH2624] | 52 | 52 | 85% | 5.00E-06 | 94% | XP_001216916.1 |
| 2 | glucose oxidase [Neosartorya udagawae] | 52 | 52 | 85% | 5.00E-06 | 94% | GAO86152.1 |
| 3 | Glucose oxidase [Rasamsonia emersonii CBS 393.64] | 51.1 | 51.1 | 100% | 9.00E-06 | 85% | KKA20115.1 |
| 4 | glucose oxidase, putative [Metarhizium acridum CQMa 102] | 51.1 | 51.1 | 85% | 9.00E-06 | 94% | XP_007809217.1 |
| 5 | glucose dehydrogenase [Colletotrichum gloeosporioides] | 51.1 | 51.1 | 85% | 9.00E-06 | 94% | AER13600.1 |
| 6 | glucose dehydrogenase [Colletotrichum gloeosporioides] | 51.1 | 51.1 | 85% | 9.00E-06 | 94% | AER13599.1 |
| 7 | glucose-methanol-choline oxidoreductase [Aureobasidium pullulans EXF-150] | 50.7 | 50.7 | 85% | 9.00E-06 | 94% | KEQ81697.1 |
| 8 | GMC oxidoreductase-like protein [Myceliophthora thermophila ATCC 42464] | 50.7 | 50.7 | 85% | 1.00E-05 | 88% | XP_003663646.1 |
| 9 | glucose-methanol-choline oxidoreductase [Zymoseptoria tritici IPO323] | 50.7 | 50.7 | 85% | 1.00E-05 | 88% | XP_003853421.1 |
| 10 | hypothetical protein BAUCODRAFT_148224 [Baudoinia compniacensis UAMH 10762] | 50.7 | 50.7 | 85% | 1.00E-05 | 88% | XP_007676619.1 |

Fig. 3

| Peak NO. | Amino acid sequence |
|---|---|
| Peak NO. 5 | GNVHIAS     SEQ ID NO: 9 |
| Peak NO. 7 | SYETKPLSTLV  SEQ ID NO: 10 |
| Peak NO. 8 | AYYWPYESR   SEQ ID NO: 11 |
| Peak NO. 10 | PAILELSGIGNPDILHK   SEQ ID NO: 12 |
| Peak NO. 11 | TLSGGKPVSYPNIYDILGDE   SEQ ID NO: 13 |
| Peak NO. 12 | AEDVQID   SEQ ID NO: 14 |
| Peak NO. 13 | FNIFPATINYEEYVR   SEQ ID NO: 15 |

Fig. 4

```
                        SEQUENCE LISTING

<160> NUMBER OF SEQ ID NOS: 15

<210> SEQ ID NO 1
<211> LENGTH: 591
<212> TYPE: PRT
<213> ORGANISM: Aspergillus iizukae

<400> SEQUENCE: 1

Met Leu Gly Lys Leu Thr Phe Phe Ser Ala Leu Ser Leu Ala Val Ala
1               5                   10                  15

Ala Pro Trp Ala Gln Pro Glu Ser Ser Tyr Asp Tyr Ile Val Ile
            20                  25                  30

Gly Gly Gly Thr Ser Gly Leu Thr Val Ala Asn Arg Leu Ser Glu Asp
            35                  40                  45

Pro Asn Val Asn Val Leu Ile Ile Glu Ala Gly Asp Ser Val Leu Asn
50                  55                  60

Asn Pro Asn Val Thr Thr Val Asp Gly Tyr Gly Leu Ala Phe Gly Thr
65                  70                  75                  80

Glu Ile Asp Trp Gln Tyr Gln Ser Val Asn Gln Thr Tyr Ala Gly Asn
                85                  90                  95

Val Pro Gln Val Leu Arg Ala Gly Lys Ala Leu Ala Gly Thr Ser Ala
            100                 105                 110

Ile Asn Gly Met Ala Tyr Thr Arg Ala Glu Asp Val Gln Ile Asp Ala
            115                 120                 125

Trp Glu Thr Ile Gly Asn Glu Gly Trp Thr Trp Lys Asn Leu Phe Pro
130                 135                 140

Tyr Tyr Leu Lys Ser Glu Asn Phe Thr Lys Pro Thr Lys Thr Gln Leu
145                 150                 155                 160

Glu Leu Gly Ala Ser Tyr Asn Leu Glu Tyr Asn Gly Glu Asn Gly Pro
                165                 170                 175

Leu Asn Val Ala Phe Thr Lys Leu Glu Ser Asn Ser Leu Thr Thr Tyr
            180                 185                 190

Leu Asn Arg Thr Phe Gln Ala Met Gly Leu Pro Trp Ser Lys Asp Leu
            195                 200                 205

Asn Gly Gly Lys Met Arg Gly Phe Asn Ile Phe Pro Ala Thr Ile Asn
210                 215                 220

Tyr Glu Glu Tyr Val Arg Glu Asp Ala Ala Arg Ala Tyr Tyr Trp Pro
225                 230                 235                 240

Tyr Glu Ser Arg Glu Asn Leu His Val Leu Leu Asn Thr Phe Ala Asn
                245                 250                 255

Arg Val Val Trp Ala Glu Gly Thr Gly Ser Gly Pro Ala Thr Ala Lys
            260                 265                 270

Gly Val Glu Val Thr Leu Lys Thr Gly Ala Ile Ser Thr Ile Gly Ala
            275                 280                 285

Thr Lys Glu Val Ile Val Ser Ala Gly Ala Leu Lys Thr Pro Ala Ile
            290                 295                 300

Leu Glu Leu Ser Gly Ile Gly Asn Pro Asp Ile Leu His Lys His Asn
305                 310                 315                 320

Ile Ser Val Lys Val Asp Leu Pro Thr Val Gly Glu Asn Leu Gln Asp
                325                 330                 335

Gln Thr Asn Ser His Met Asp Ala Ser Ser Asn Arg Thr Leu Ser Gly
            340                 345                 350
```

```
Gly Lys Pro Val Ser Tyr Pro Asn Ile Tyr Asp Ile Leu Gly Asp Glu
            355                 360                 365

Ala Glu Thr Val Gly Asn Lys Leu Arg Ala Asn Leu Lys Lys Tyr Ala
        370                 375                 380

Glu Glu Ser Ala Lys Ala Asn Gly Asn Val Met Lys Ala Ala Asp Leu
385                 390                 395                 400

Glu Arg Leu Phe Glu Val Gln Tyr Asp Leu Ile Phe Lys Lys Asn Thr
                405                 410                 415

Pro Val Ala Glu Ile Leu Asn Tyr Ala Ala Asp Lys Thr Leu Ser Thr
            420                 425                 430

Glu Phe Trp Ser Leu Leu Pro Phe Ala Arg Gly Asn Val His Ile Ala
        435                 440                 445

Ser Ala Asn Pro Lys Gln Phe Pro Thr Ile Asn Pro Asn Tyr Phe Met
450                 455                 460

Phe Glu Trp Asp Val Glu Ser Phe Ala Ala Val Gly Gln Tyr Ile Arg
465                 470                 475                 480

Arg Ser Tyr Glu Thr Lys Pro Leu Ser Thr Leu Val Lys Glu Ala Thr
                485                 490                 495

Pro Gly Leu Lys Asn Val Pro Gln Asp Ala Ser Val Glu Gln Trp Lys
            500                 505                 510

Glu Trp Val Phe Asp Gly Asn Tyr Arg Ser Asn Phe His Pro Val Gly
        515                 520                 525

Thr Ala Ala Met Met Pro Arg Ala Met Gly Gly Val Val Asp Asn Arg
530                 535                 540

Leu Lys Val Tyr Gly Thr Ser Asn Val Arg Val Val Asp Ala Ser Ala
545                 550                 555                 560

Leu Pro Tyr Gln Val Cys Gly His Leu Val Ser Thr Leu Tyr Ala Val
                565                 570                 575

Ala Glu Arg Ala Ala Glu Leu Ile Lys Ala Asp Ala Ala Val
            580                 585                 590

<210> SEQ ID NO 2
<211> LENGTH: 1776
<212> TYPE: DNA
<213> ORGANISM: Aspergillus iizukae

<400> SEQUENCE: 2
atgttgggca aactcacgtt ctttagtgcc ctgtcactgg cagtggctgc tccctgggca      60
cagcccgaat cgtccagtta tgattatatc gtcattggag gaggtaccag tggtcttacc     120
gttgccaacc gtctgtctga agaccccaat gtcaacgtgc tcattatcga ggctggagac     180
tcggttttga ataacccgaa tgtcacaaca gtcgatggct acggacttgc attcgggaca     240
gagatagatt ggcagtacca atctgttaac cagacctatg ctggaaatgt tccccaggtg     300
cttcgtgctg aaaggcctt ggctgggaca agtgccatca acggcatggc ttatactcgc      360
gcagaagatg ttcagatcga tgcttgggag actatcggta tgaaggctg acctggaag       420 aatctcttcc cttactacct gaagagcgag aacttcacca gcctaccaa gacccagctc      480 gagctaggag cctcgtataa tcttgaatac aatggcgaaa acgtcctct caacgtcgct      540 tttaccaagc tcgaatctaa cagcttgact acctacctca accgtacgtt ccaagccatg     600
ggcctcccat ggtccaaaga tctcaacggt ggaaagatgc gcggcttcaa catcttcccg     660
gctacaatca actacgaaga atacgttcgt gaggatgctg cccgtgcata ctactggcct     720
tatgagtccc gtgagaactt gcatgtgctg ctcaacaccct ttgccaatag agtcgtgtgg    780
```

```
gctgaaggaa ctggcagtgg gccggccact gccaaggtg tggaagtcac tttgaaaact      840
ggcgccatca gcactattgg cgctaccaag gaagtgattg tctctgctgg tgccctgaag     900
accccctgcga ttctcgagct ttccggcatc ggcaaccccg acatcctcca taaacacaac   960
atctctgtta aggtcgactt gcccactgtc ggtgagaacc tccaggacca gacgaatagt   1020
cacatggatg cctccagcaa ccgcactctc tccggtggaa agcctgtctc ctaccccaac   1080
atctacgata ttctcggaga cgaggctgag actgtcggca acaagcttcg cgccaacttg   1140
aagaagtatg ccgaggaatc agccaaggcc aatggcaatg tcatgaaggc tgccgatctt   1200
gaacgcctct tcgaggtgca gtacgatctc atttttcaaga agaataccccc tgtcgctgag  1260
atcctgaact acgctgctga caaaaccctg tctacggaat tctggtccct acttccttt    1320
gctcgtggaa acgtccatat cgcatccgca aacccgaagc agtttcccac gatcaaccct   1380
aattacttca tgttcgagtg ggatgtcgag agctttgctg cggtcggaca atacatccgt   1440
cgttcgtatg agaccaagcc tctcagcact ctggtcaagg aagcgactcc tggtctcaag   1500
aatgttcctc aggacgcttc ggtggagcag tggaaggagt gggtgtttga cggtaactat   1560
cgttccaact ccaccctgt tggcaccgct gctatgatgc cccgcgctat gggcggtgtt    1620
gtcgacaacc gcctcaaggt gtatggcact tctaacgtca gagttgtgga tgcttcggcg   1680
ctcccttacc aggtctgtgg tcacctagtg agcaccctct atgctgtggc ggagcgggct   1740
gccgaattga tcaaggccga tgctgctgct gtgtag                              1776
```

<210> SEQ ID NO 3
<211> LENGTH: 20
<212> TYPE: PRT
<213> ORGANISM: Aspergillus iizukae

<400> SEQUENCE: 3

Ser Ser Ser Tyr Asp Tyr Ile Val Ile Gly Gly Gly Thr Ser Gly Leu
1               5                   10                  15

Thr Val Ala Asn
        20

<210> SEQ ID NO 4
<211> LENGTH: 35
<212> TYPE: DNA
<213> ORGANISM: Artificial Sequence
<220> FEATURE:
<223> OTHER INFORMATION: Primer GDH5453-F
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

```
<400> SEQUENCE: 4
taygaytaya thgtnathgg nggnggnacn wsngg                              35

<210> SEQ ID NO 5
<211> LENGTH: 21
<212> TYPE: DNA
<213> ORGANISM: Artificial Sequence
<220> FEATURE:
<223> OTHER INFORMATION: Primer GDH5453-5-1-R
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 5
nswngcdatr tgnacrttnc c                                            21

<210> SEQ ID NO 6
<211> LENGTH: 1298
<212> TYPE: DNA
<213> ORGANISM: Artificial Sequence
<220> FEATURE:
<223> OTHER INFORMATION: PCR product

<400> SEQUENCE: 6
tgttgcgatg tgaacgttgc caaccgtctg tctgaagacc ccaatgtcaa cgtgctcatt    60
atcgaggctg gagactcggt tttgaataac ccgaatgtca acagtcgat ggctacgga    120 cttgcattcg ggacagagat agattggcag taccaatctg ttaaccagac ctatgctgga   180
aatgttcccc aggtgcttcg tgctggaaag gccttggctg gacaagtgc catcaacggt    240 acgtaccgtc gtcaacatat agtcggttca aggctaacgc gtccatctcc ttaggcatgg   300
cttatactcg cgcagaagat gttcagatcg atgcttggga gactatcggt aatgaaggct   360
ggacctggaa gaatctcttc ccttactacc tgaagagcga gaacttcacc aagcctacca   420
agacccagct cgagctagga gcctcgtata atcttgaata caatggcgaa aacggtcctc   480
tcaacgtcgc ttttaccaag ctcgaatcta acagcttgac tacctacctc aaccgtacgt   540
tccaagccat gggcctccca tggtccaaag atctcaacgg tggaaagatg cgcggcttca   600
acatcttccc ggctacaatc aactacgaag aatacgttcg tgaggatgct gcccgtgcat   660
actactggcc ttatgagtcc cgtgagaact tgcatgtgct gctcaacacc tttgccaata   720
gagtcgtgtg ggctgaagga actggcagtg ggccggccac tgccaaaggt gtggaagtca   780 cttttgaaaac tggcgccatc agcactattg gcgctaccaa ggaagtgatt gtctctgctg   840
gtgccctgaa gaccctgcg attctcgagc tttccggcat cggcaacccc gacatcctcc    900
ataaacacaa catctctgtt aaggtcgact tgcccactgt cggtgagaac ctccaggacc   960
agacgaatag tcacatggat gcctccagca accgcactct ctccggtgga aagcctgtct  1020
cctaccccaa catctacgat attctcggag acgaggctga gactgtcggc aacaagcttc  1080
gcgccaactt gaagaagtat gccgaggaat cagccaaggc caatggcaat gtcatgaagg  1140
```

```
ctgccgatct tgaacgcctc ttcgaggtgc agtacgatct cattttcaag aagaataccc    1200
ctgtcgctga gatcctgaac tacgctgctg acaaaaccct gtctacggaa ttctggtccc    1260
tacttccttt tgctcgtgga aacgtccaca tagcaacc                            1298
```

<210> SEQ ID NO 7
<211> LENGTH: 20
<212> TYPE: DNA
<213> ORGANISM: Artificial Sequence
<220> FEATURE:
<223> OTHER INFORMATION: Primer FS51R07F

<400> SEQUENCE: 7

```
aaccgtctgt ctgaagaccc                                                20
```

<210> SEQ ID NO 8
<211> LENGTH: 16
<212> TYPE: DNA
<213> ORGANISM: Artificial Sequence
<220> FEATURE:
<223> OTHER INFORMATION: Primer FS51R07R

<400> SEQUENCE: 8

```
tacttccttt tgctcg                                                    16
```

<210> SEQ ID NO 9
<211> LENGTH: 7
<212> TYPE: PRT
<213> ORGANISM: Aspergillus iizukae

<400> SEQUENCE: 9

Gly Asn Val His Ile Ala Ser
1               5

<210> SEQ ID NO 10
<211> LENGTH: 11
<212> TYPE: PRT
<213> ORGANISM: Aspergillus iizukae

<400> SEQUENCE: 10

Ser Tyr Glu Thr Lys Pro Leu Ser Thr Leu Val
1               5                   10

<210> SEQ ID NO 11
<211> LENGTH: 9
<212> TYPE: PRT
<213> ORGANISM: Aspergillus iizukae

<400> SEQUENCE: 11

Ala Tyr Tyr Trp Pro Tyr Glu Ser Arg
1               5

<210> SEQ ID NO 12
<211> LENGTH: 17
<212> TYPE: PRT
<213> ORGANISM: Aspergillus iizukae

<400> SEQUENCE: 12

Pro Ala Ile Leu Glu Leu Ser Gly Ile Gly Asn Pro Asp Ile Leu His
1               5                   10                  15
Lys

```
<210> SEQ ID NO 13
<211> LENGTH: 20
<212> TYPE: PRT
<213> ORGANISM: Aspergillus iizukae

<400> SEQUENCE: 13

Thr Leu Ser Gly Gly Lys Pro Val Ser Tyr Pro Asn Ile Tyr Asp Ile
1               5                   10                  15

Leu Gly Asp Glu
            20

<210> SEQ ID NO 14
<211> LENGTH: 7
<212> TYPE: PRT
<213> ORGANISM: Aspergillus iizukae

<400> SEQUENCE: 14

Ala Glu Asp Val Gln Ile Asp
1               5

<210> SEQ ID NO 15
<211> LENGTH: 15
<212> TYPE: PRT
<213> ORGANISM: Aspergillus iizukae

<400> SEQUENCE: 15

Phe Asn Ile Phe Pro Ala Thr Ile Asn Tyr Glu Glu Tyr Val Arg
1               5                   10                  15
```

GLUCOSE DEHYDROGENASE

TECHNICAL FIELD

The present invention relates to a novel glucose dehydrogenase, and more specifically to an *Aspergillus* genus-derived flavin adenine dinucleotide (FAD) dependent glucose dehydrogenase (E.C.1.1.99.10) and its genes. The present application claims priority based on Japanese Patent Application No. 2015-218852 filed on Nov. 6, 2015, and and the content of the patent application is hereby incorporated by reference herein in its entirety.

BACKGROUND ART

Diabetics are increasing year by year, and diabetics, particularly insulin-dependent patients require daily monitoring of the blood glucose level and control of the blood glucose. In recent years, the blood glucose level of diabetics can be checked by a self blood glucose measuring instrument which can simply and accurately measure the blood glucose level using an enzyme in real time. For glucose sensors (for example, a sensor used for a self blood glucose measuring instrument), a glucose oxidase (E.C.1.1.3.4), a PQQ-dependent glucose dehydrogenase (E.C.1.1.5.2) (for example, see Patent Literatures 1 to 3) have been developed, but they have problems with oxygen reactivity, and reactivity to maltose and galactose. In order to solve these problems, FAD-dependent glucose dehydrogenase (hereinafter abbreviated as "FAD-GDHs") has been developed (for example, see Patent Literatures 4, 5, and Non-Patent Literatures 1 to 4).

Commonly, in an examination for judging diabetes, not only oral glucose tolerance test, but also oral xylose load test, and transvenous xylose load test are performed. It is known that FAD-GDH generally reacts to xylose, so that the use of FAD-GDH has a problem of affection on the blood glucose level in the above-mentioned load test.

CITATION LIST

Patent Literature

[PTL 1] Japanese Unexamined Patent Application Publication No. 2000-350588
[PTL 2] Japanese Unexamined Patent Application Publication No. 2001-197888
[PTL 3] Japanese Unexamined Patent Application Publication No. 2001-346587
[PTL 4] PCT International Publication No. 2004/058958
[PTL 5] PCT International Publication No. 2007/139013
[PTL 6] PCT International Publication No. 2015/060150

Non Patent Literature

[NPL 1] Studies on the glucose dehydrogenase of *Aspergillus oryzae*. I. Induction of its synthesis by p-benzoquinone and hydroquinone, T. C. Bak, and R. Sato, Biochim. Biophys. Acta, 139, 265-276 (1967).
[NPL 2] Studies on the glucose dehydrogenase of *Aspergillus oryzae*. II. Purification and physical and chemical properties, T. C. Bak, Biochim. Biophys. Acta, 139, 277-293 (1967).
[NPL 3] Studies on the glucose dehydrogenase of *Aspergillus oryzae*. III. General enzymatic properties, T. C. Bak, Biochim. Biophys. Acta, 146, 317-327 (1967).
[NPL 4] Studies on the glucose dehydrogenase of *Aspergillus oryzae*. IV. Histidyl residue as an active site, T.C. Bak, and R. Sato, Biochim. Biophys. Acta, 146, 328-335 (1967).

SUMMARY OF INVENTION

Technical Problem

FAD-GDH has a problem of reactivity to xylose, but has marked substrate specificity, and is regarded as a promising enzyme for a glucose sensor. For commercialization of FAD-GDH, as mentioned above, there is a problem of reactivity to xylose. In view of the above-mentioned circumstances, the present invention is intended to provide a highly practical novel FAD-GDH for a glucose sensor and the uses thereof. FAD-GDH having low reactivity to xylose is reported (PTL 6), but the properties such as pH stability, which are particularly important when it is used in a glucose sensor, are not clear, so that its practical value is unknown.

Solution to Problem

In order to solve the above-mentioned problems, the inventors have carried out an extensive screening of a wide range of microorganisms. As a result of this, they have succeeded in obtaining novel FAD-GDH having low reactivity to xylose. The properties of the FAD-GDH have been studied, and, amazingly, it has been found to exhibit high activity in a wide range of pH range including the optimum pH of the mediator (potassium ferricyanide) frequently used in glucose sensors. This fact indicates that the FAD-GDH is suitable for the use in a glucose sensor, and has high practicality.

The following aspects of the invention are based on the above-mentioned results and discussions.

[1] A glucose dehydrogenase including the following properties:
(1) action: catalyzes the reaction of oxidizing hydroxyl groups of glucose to form glucono-δ-lactone in the presence of an electron acceptor;
(2) substrate specificity: reactivity to D-xylose is 10% or less when the reactivity to D-glucose is 100%;
(3) pH stability: stable at pH 5 to 8; and
(4) amino acid sequence: including the amino acid sequence set forth in SEQ ID NO: 1, or an amino acid sequence with an identity of 83% or more to the amino acid sequence.

[2] The glucose dehydrogenase according to [1], wherein the amino acid sequence is an amino acid sequence with an identity of 90% or more to the amino acid sequence set forth in SEQ ID NO: 1.

[3] A glucose dehydrogenase including the following properties:
(1) action: catalyzes the reaction of oxidizing hydroxyl groups of glucose to form glucono-δ-lactone in the presence of an electron acceptor;
(2) substrate specificity: reactivity to D-xylose is 10% or less when the reactivity to D-glucose is 100%;
(3) pH stability: stable at pH 5 to 8; and
(4) molecular weight: about 60 kDa (as measured by SDS-PAGE).

[4] The glucose dehydrogenase according to [3] further having the following enzymatic properties:
(5) optimum pH: 7.0;
(6) optimum temperature: 50° C.; and
(7) thermostability: stable in the range of 20° C. to 50° C. (pH 5.0, 1 hour).

[5] The glucose dehydrogenase according to any one of [1] to [4], wherein in the substrate specificity, the reactivity to D-xylose is 8% or less when the reactivity to D-glucose is 100%.

[6] The glucose dehydrogenase according to any one of [1] to [5], which is an enzyme derived from *Aspergillus iizukae*.

[7] The glucose dehydrogenase according to [6], wherein the *Aspergillus iizukae* is the *Aspergillus iizukae* NBRC 8869 strain.

[8] A glucose dehydrogenase gene including any DNA selected from the group consisting of the following (A) to (C):

(A) a DNA coding the amino acid sequence set forth in SEQ ID NO: 1;

(B) a DNA composed of the base sequence set forth in SEQ ID NO: 2; and (C) a DNA having a base sequence equivalent to the base sequence set forth in SEQ ID NO: 2, and coding a protein having glucose dehydrogenase activity.

[9] A recombinant DNA including the glucose dehydrogenase gene according to [8].

[10] A microorganism holding the recombinant DNA according to [9].

[11] A method for producing glucose dehydrogenase including the following steps (1) and (2), or the following steps (i) and (ii):

(1) a step of culturing an *Aspergillus iizukae* NBRC 8869 strain; and (2) a step of collecting glucose dehydrogenase from the culture solution and/or bacterial cells after culturing;

(i) a step of culturing the microorganism according to [10] under conditions where the protein coded by the above-mentioned gene is produced; and (ii) a step of collecting the protein produced.

[12] A method for measuring glucose including measuring the glucose in a sample using the glucose dehydrogenase according to any one of [1] to [7].

[13] A glucose measuring reagent including the glucose dehydrogenase according to any one of [1] to [7].

[14] A kit for measuring glucose including the glucose measuring reagent according to [13].

[15] A glucose sensor including the glucose dehydrogenase according to any one of [1] to [7].

[16] An enzyme preparation including the glucose dehydrogenase according to any one of [1] to [7].

BRIEF DESCRIPTION OF DRAWINGS

FIG. 3 The result of BLAST analysis using the N-terminal amino acid sequence as an inquiry sequence.

FIG. 4 The result of the analysis of internal amino acid sequence. The amino acid sequences of the peaks obtained by HPLC separation are given.

DESCRIPTION OF EMBODIMENTS

1. Term

Figure 1:
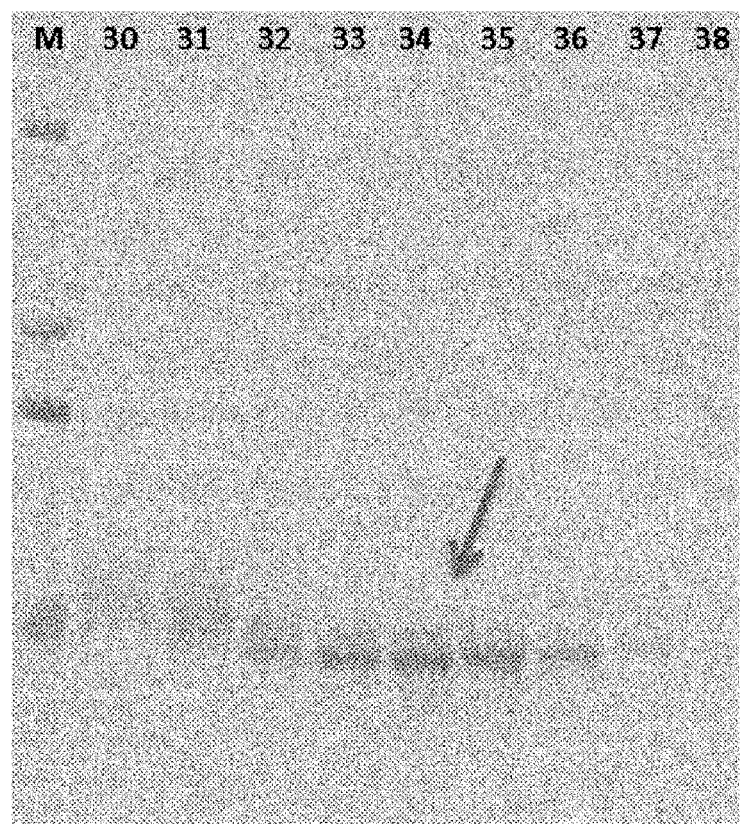
FIG. 1 The result of the analysis of the enzyme (purified enzyme) purified from a culture solution of the *Aspergillus iizukae* No. 5453 strain by SDS-PAGE. M represents molecular weight markers (200, 116, 97.2, and 66.4 KDa from the top), and the lane number is the fraction number when separated by Superdex 200.

In the present description, the terms "isolated" and "purified" are used interchangeably. The term "isolated" is used for distinction from the natural state, more specifically, the state existing in nature. The artificial operation of isolation makes the "isolated state", which is different from the natural state. What is isolated is clearly and definitely different from natural product itself.

The purity of the isolated enzyme is not particularly limited. However, when the enzyme is intended to be used in an application where high purity is demanded, the purity of the isolated enzyme is preferably high.

2. Glucose Dehydrogenase and Bacterium Producing the Same

A first aspect of the present invention provides a glucose dehydrogenase and a bacterium producing the same. The glucose dehydrogenase of the present invention (hereinafter may be referred to as "the present enzyme") includes the following properties. Firstly, the present enzyme catalyzes the following reaction, more specifically, the reaction of oxidizing hydroxyl groups of glucose in the presence of an electron acceptor to form glucono-δ-lactone. On the other hand, the present enzyme has marked substrate specificity, and selectively acts on D-glucose. More specifically, the present enzyme has low reactivity to D-xylose. Specifically, the reactivity to D-xylose is 10% or less when the reactivity to D-glucose is 100%. Preferably, the reactivity is 8% or less. More preferably, the reactivity is 7% or less.

On the other hand, the present enzyme has extremely low reactivity to maltose and D-galactose. The reactivity to maltose when the reactivity to D-glucose is 100%, and the reactivity to D-galactose when the reactivity to D-glucose is 100% are 5% or less, and preferably 3% or less. Even more preferably, the reactivity is 1% or less. Yet even more preferably, the reactivity is substantially 0% (more specifically, it has no substantial reactivity to maltose and galactose).

The present enzyme having the above-mentioned marked substrate specificity is preferred as an enzyme for accurately measuring the glucose amount in the sample. More specifically, the present enzyme allows the amount of the target glucose to be measured more accurately even when impurities such as D-xylose, maltose, or D-galactose are included in the sample. Accordingly, the present enzyme is suitable for the use where the presence of such impurities in the sample is anticipated or concerned (typically the measurement of the glucose amount in the blood), and is applicable to various uses including this one, more specifically, has high versatility. The reactivity and substrate specificity of the present enzyme can be measured and evaluated by the method given in the below-described Example.

The origin of the present enzyme, more specifically the bacterium producing the present enzyme is *Aspergillus iizukae*. The bacterium is not limited as long as it can produce the present enzyme having the above-mentioned properties. A specific example of the producing bacterium is NBRC 8869 strain (the same strain as the *Aspergillus iizukae* No. 5453 strain used in Example). This strain is deposited in NITE Biological Resource Center (NBRC) (2-5-8 Kazusakamatari, Kisarazu, Chiba, 292-0818), and can be purchased through a predetermined procedure.

The producing bacterium may be a wild strain (a strain isolated from nature, which has been not subjected to mutation or modification such as gene manipulation), or a mutant. Alternatively, the producing bacterium may be a transformant obtained by introducing the gene of the present enzyme into a host microorganism.

Another property of the present enzyme is that it has marked pH stability. Specifically, the present enzyme is stable at pH 5.0 to 8.0. More specifically, when the pH of the enzyme solution subjected to the treatment is within this range, it keeps 50% or more, preferably 60% or more, and more preferably 70% or more of activity after treatment at 37° C. for 1 hour. Preferably, the high activity is kept in the range of pH 5.0 to 9.0, pH 4.0 to 9.0 or pH 4.0 to 10.0. The property of "being stable at pH 5.0 to 8.0" means that high activity is maintained in at least the pH range, and does not mean that the activity necessarily decreases outside the pH range (for example, pH 4.5).

In one embodiment, the polypeptide chain which consists of the present enzyme has an amino acid sequence set forth in SEQ ID NO: 1 or an equivalent amino acid sequence. The "equivalent amino acid sequence" herein denotes an amino acid sequence that is partly different from the amino acid sequence set forth in SEQ ID NO: 1 but this difference does not have a substantial effect on the function (herein, the glucose dehydrogenase activity) of the protein. Thus, an enzyme which has a polypeptide chain consisting of the equivalent amino acid sequence shows a glucose dehydrogenase activity. The term "glucose dehydrogenase activity" denotes an activity of catalyzing the reaction which generates glucono-δ-Lactone by oxidation of hydroxyl groups of glucose. However, the degree of the activity is not particularly limited as long as the function of glucose dehydrogenase can be exhibited. However, it is preferable that the activity is equal to or higher than that of the enzyme having the polypeptide chain which consists of the amino acid sequence set forth in SEQ ID NO: 1.

The "partial difference in the amino acid sequence" typically denotes that mutation (change) occurs in an amino acid sequence due to deletion or substitution of one to several amino acids constituting the amino acid sequence, or addition or insertion of one to several amino acids, or the combination thereof. Herein, the difference in the amino acid sequence is permitted as long as the glucose dehydrogenase activity is maintained (more or less change in the activity is permitted). As long as this condition is satisfied, the position in which a difference in the amino acid sequence occurs is not particularly limited and the difference may occur in a plurality of positions. The plurality herein signifies a numerical value corresponding to less than about 30%, preferably less than about 20%, further preferably less than about 10%, still further preferably less than about 5%, and most preferably less than about 1% with respect to the total amino acid. That is to say, the equivalent protein has, for example, about 83% or more, preferably about 85% or more, further preferably about 90% or more, more and more preferably about 95% or more, still further preferably about 98% or more and most preferably about 99% or more identity to the amino acid sequence set forth in SEQ ID NO: 1. It is preferable histidine (H) at the position 425 and histidine (H) at the position 568, which are deduced to form the active center, are not subjected to the deletion or substitution.

Preferably, an equivalent protein is obtained by allowing conservative amino acid substitution to be generated in an amino acid residue that is not essential to the glucose dehydrogenase activity. Herein, "conservative amino acid substitution" denotes substitution of an amino acid residue to an amino acid residue having a side chain of the same property. The amino acid residue is classified into some families according to its side chain, for example, the basic side chain (for example, lysin, arginine, and histidine), the acid side chain (for example, asparatic acid, and glutamic acid), the uncharged polar side chain (for example, glycine, asparagine, glutamine, serine, threonine, tyrosine, and cysteine), the nonpolar side chain (for example, alanine, valine, leucine, isoleucine, proline, phenyl alanine, methionine, and tryptophane), branched side chain (for example, threonine, valine, and isoleucine), and the aromatic side chain (for example, tyrosine, phenyl alanine, tryptophane, and histidine). The conservative amino acid substitution is carried out between the amino acid residues in the same family.

The identity (%) between two amino acid sequences or two nucleic acids (hereinafter, referred to as "two sequences" as a term including the both) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain a nucleotide sequence equivalent to the nucleic acid molecule of the present invention, for example, BLAST nucleotide search with score=100 and word length=12 may be carried out by the NBLAST program. In order to obtain an amino acid sequence equivalent to the polypeptide molecule of the present invention, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. Another example of the mathematical algorithm that can be used for comparing sequences includes an algorithm described in Meyers and Miller (1988) Comput.

Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. Furthermore, the homology between two nucleic acid sequences can be determined using the GAP program in the GCG software package with the gap weight of 50 and the gap length weight of 3.

The molecular weight of the present enzyme is about 60 kDa (see the below-described Example). The molecular weight was measured by SDS-PAGE.

The present enzyme may be a part of a larger protein (for example, fusion protein). Examples of a sequence to be added in the fusion protein may include a sequence useful for purification, for example, a sequence of a multi histidine residue, and an additional sequence for securing the stability for producing a recombinant, and the like.

The present enzyme having the above-mentioned amino acid sequence can be prepared easily by a genetic engineering technique. For example, the present enzyme can be prepared by transforming an appropriate host cell (for example, *Escherichia coli*) by DNA encoding the present enzyme, and by collecting proteins expressed in the transformant. The collected proteins are appropriately purified according to the purposes. In the case where the present enzyme is prepared as a recombinant protein, various modifications can be carried out. For example, DNA encoding the present enzyme and other appropriate DNA are inserted into the same vector and the vector is used for producing a recombinant protein. Then, the enzyme consisting of a recombinant protein to which arbitrary peptide or protein is linked can be obtained. Furthermore, modification may be carried out so as to cause addition of sugar chain and/or lipid or processing of N-terminal or C-terminal. The above-mentioned modification permits extraction of a recombinant protein, simplification of purification, addition of biological functions, or the like.

The present enzyme can be further characterized by the following enzymological properties (optimum pH, optimum temperature, and thermostability).

The optimum pH is 7.0. The optimum pH is, for example, determined based on the result measured in a 0.1 M acetic acid buffer in the pH range of pH 5.0 to 5.5, in a 0.1 M MES buffer in the pH range of pH 5.5 to 6.5, in a 0.1 M phosphate buffer in the pH range of pH 6.0 to 8.0, and in a 0.1 M Tris buffer in the pH range of pH 8.0 to 9.0.

The optimum temperature is 50° C. The optimum temperature can be evaluated based on the measurement result under the condition of pH 7.0 (for example, a 0.1 M phosphate buffer is used).

Regarding the thermostability, activity of 80% or more is maintained even after treatment in an acetic acid buffer (pH 5.0) at 20° C. to 50° C. for 1 hour.

3. DNA Coding for Glucose Dehydrogenase

The second aspect of the present invention provides a nucleic acid relating to the present enzyme. That is, provided are a gene coding for the present enzyme, a nucleic acid that can be used as a probe for identifying a nucleic acid coding for the present enzyme, and a nucleic acid that can be used as a primer for amplifying or mutating a nucleic acid coding for the present enzyme. In one embodiment, the gene of the present invention consists of a DNA coding for the amino acid sequence set forth in SEQ ID NO: 1. The example of the embodiment is a DNA having a nucleotide sequence set forth in SEQ ID NO: 2.

The gene coding for the present enzyme is typically used in preparation of the present enzyme. According to a genetic engineering procedure using the gene coding for the present enzyme, the present enzyme in a more homogeneous state can be obtained. Further, the method can be a preferable method also in the case of preparing a large amount of the present enzyme. Note that uses of the gene coding for the present enzyme are not limited to preparation of the present enzyme. For example, the nucleic acid can also be used as a tool for an experiment intended for clarification of action mechanisms of the present enzyme or a tool for designing or preparing a mutant (modified form) of the present enzyme.

The "gene coding for the present enzyme" herein refers to a nucleic acid capable of obtaining the present enzyme when it is expressed, and includes, as a matter of course of a nucleic acid having a nucleotide sequence corresponding to the amino acid sequence of the present enzyme, also a nucleic acid obtained by adding a sequence that does not code for an amino acid sequence to such a nucleic acid. Degeneracy of a codon is also considered.

The nucleic acid of the present invention can be prepared in an isolated state by use of a standard genetic engineering technique, molecular biological technique, biochemical technique, chemical synthesis, PCR (e.g. overlap PCR) and the like in reference to the present specification or the sequence information disclosed in the appended sequence listing.

Another embodiment of the present invention provides a nucleic acid different in a nucleotide sequence in a part (hereinafter also referred to as a "equivalent nucleic acid", and a nucleotide sequence defining an equivalent nucleic acid is also referred to as a "equivalent nucleotide sequence") as compared to the nucleotide sequence of the gene coding for the present enzyme, although functions of a protein coded by the nucleic acid are equal. An example of the equivalent nucleic acid includes a DNA composed of a nucleotide sequence containing substitution, deletion, insertion, addition or inversion of 1 to several nucleotides on the basis of the nucleotide sequence of the nucleic acid coding for the present enzyme and coding for a protein having enzyme activity characteristic to the present enzyme (i.e. glucose dehydrogenase activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases. The equivalent nucleic acid has, for example, about 60% or more, preferably about 70% or more, further preferably about 80% or more, more and more preferably about 85% or more, still further preferably about 90% or more, further and further preferably about 95% or more and most preferably about 99% or more identity to the standard nucleic sequence (SEQ ID NO: 2).

Such an equivalent nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The equivalent nucleic acid can be obtained also in other methods such as exposure to ultraviolet radiation.

Another embodiment of the present invention relates to a nucleic acid having the complementary nucleotide sequence to the nucleotide sequence of the gene coding for the present enzyme of the present invention. Another embodiment of the present invention provides a nucleic acid having a nucleotide sequence with an identity of at least about 60%, 70%, 80%, 90%, 95%, 99%, or 99.9% to the nucleotide sequence of the gene coding for the present enzyme of the present invention or the complementary nucleotide sequence Another embodiment of the present invention relates to a nucleic acid having a nucleotide sequence hybridizing to the complementary nucleotide sequence to the nucleotide sequence of the gene coding for the present enzyme of the invention or its homologous nucleotide sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), 5×Denhardt solution, 1% SDS, 10% dextran sulfate, 10 µg/ml of denatured salmon sperm DNA, and 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), 1×Denhardt solution, 1% SDS, 10% dextran sulfate, 10 µg/ml of denatured salmon sperm DNA, and 50 mM phosphate buffer (pH 7.5) as hybridization liquid.

Another embodiment of the present invention provides a nucleic acid (nucleic acid fragment) having a part of the nucleotide sequence of the gene coding for the present enzyme of the invention or the complementary nucleotide sequence. Such a nucleic acid fragment can be used in detection, identification, and/or amplification of a nucleic acid having the nucleotide sequence of the gene coding for the present enzyme of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the nucleotide sequence of the gene coding for the present enzyme of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for the present enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a modified enzyme can be used. Examples of *Escherichia coli* include *Escherichia coli* BL21 (DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Feigner, P. L. et al., Proc. Natl. Acad. Sci. U.S.A. 84, 7413-7417 (1984)). Note that the microorganism of the present invention can be used in producing the present enzyme of the present invention.

4. Manufacturing Method of Glucose Dehydrogenase

A further aspect of the present invention provides a manufacturing method of glucose dehydrogenase. In one embodiment of the manufacturing method of the present invention, a step of culturing *Aspergillus iizukae* No. 545B strain (step (1)), and a step of collecting the glucose dehydrogenase from a culture solution and/or a cell body after culture (step (2)) are carried out.

The culturing method and the culture conditions are not particularly limited as long as the target enzyme is produced. That is to say, on the condition that the glucose dehydrogenase is produced, a methods and culture conditions suitable for culturing of microorganisms to be used can be set appropriately. Examples of media, culturing temperature and culture period are described below.

Any media can be used as long as microorganisms to be used can grow. For example, a medium containing a carbon source such as glucose, sucrose, gentiobiose, soluble starch, glycerin, dextrin, syrup, and organic acids; a nitrogen source such as ammonium sulfate, ammonium carbonate, ammonium phosphate, ammonium acetate, or peptone, yeast extract, corn steep liquor, casein hydrolysate, bran, meat extract, and the like; and further, inorganic salts such as potassium salt, magnesium salt, sodium salt, phosphate salt, manganese salt, iron salt, and zinc salt, can be used. In order to promote the growth of microorganisms to be used, vitamin, amino acid, and the like may be added to the medium. The pH of the medium is adjusted to, for example, about 3 to 8, and preferably, about 5 to 7. The culturing temperature is generally about 10° C. to 50° C., and preferably about 25° C. to 35° C. The culturing is carried out for one to fifteen days, preferably two to five days under aerobic conditions. As a culturing method, for example, a shake culture method, and an aerobic submerged culture method with a jar fermenter can be employed.

After the culturing in the above-mentioned conditions, glucose dehydrogenase is collected from the culture solution or the cell body (step (2)). When glucose dehydrogenase is collected from the culture solution, the present enzyme can be obtained by separation and purification after removing insoluble matters by, for example, filtration (e.g. diatomaceous earth filtration), centrifugation of culture supernatant followed by carrying out any combinations of concentration by ultrafiltration membrane, salting out of ammonium sulfate precipitation, dialysis, various types of chromatography. On the other hand, when the present enzyme is collected from the cell body, the present enzyme can be obtained by pulverizing the cell body by pressuring treatment, ultrasonication, treatment with beads and the like, followed by separation and purification thereof similar to the above. Note here that the above-mentioned series of processes (pulverizing of cell body, separation, and purification) may be carried out after the cell body is collected from a culture solution by filtration, centrifugation, and the like. Note here that, in general, fractionation is conducted in each purification step by using activity as an indicator and then go forward, except for a case where suitable conditions can be set, for example, by a preliminary experiment.

According to another embodiment of the present invention, glucose dehydrogenase is manufactured by using the above-mentioned transformant. In the manufacturing method in this embodiment, firstly, the above-mentioned transformant is cultured in the conditions in which the protein encoded by the introduced gene is produced (step (i)). As to various vector-host systems, the culture conditions for transformant are well-known, and a person skilled in the art can set appropriate culture conditions easily. After the culturing step, a step of collecting the produced protein (i.e., glucose dehydrogenase) is carried out (step (ii)). Collection and the following purification may be carried out by the same method as mentioned in the above-mentioned embodiment.

The degree of purification of the enzyme is not particularly limited; for example, the enzyme can be purified to specific activity of 10 to 1000 (U/mg), preferably specific activity of 50 to 500 (U/mg). Additionally, the final form may be liquid or solid (including powder).

5. Use of Glucose Dehydrogenase

Another aspect of the present invention relates to the use of the present enzyme. This aspect provides, firstly, a method for measuring glucose using the present enzyme. The glucose measurement method of the present invention measures the glucose amount in a sample using oxidation-reduction reaction by the present enzyme. The present invention can be applied to various uses where the change by this reaction can be used.

The present invention is used for, for example, the measurement of blood glucose level, and the measurement of glucose concentration in food (for example, condiments and beverages). Additionally, the present invention may be used for examining the degree of fermentation in the manufacturing process of a fermented food (for example, vinegar) or a fermented beverage (for example, beer or sake).

The present invention also provides a glucose measuring reagent including the present enzyme. The reagent is used in the above-mentioned glucose measurement method of the present invention. For the purpose of stabilization of the glucose measuring reagent and activation during use, for example, a serum albumin, a protein, a surfactant, a saccharide, a glycitol, or an inorganic salt may be added.

The glucose measuring reagent may be a component of a measuring kit. In other words, the present invention also provides a kit including the above-mentioned glucose measuring reagent (glucose measuring kit). The kit of the present invention includes the above-mentioned glucose measuring reagent as an essential component. It also includes, for example, a reaction reagent, a buffer solution, a glucose standard solution, and a container as optional elements. The glucose measuring kit of the present invention usually includes an instruction.

A glucose sensor can be composed using the present enzyme. More specifically, the present invention also provides a glucose sensor including the present enzyme. According to a typical structure of the glucose sensor of the present invention, an electrode system including a working electrode and a counter electrode are formed on an insulating substrate, and a reagent layer including the present enzyme and a mediator is formed on the electrode system. A measurement system further including a reference electrode may be used. The use of a so-called three-electrode measurement system allows indicating the potential of the working electrode based on the potential of the reference electrode. The materials of these electrodes are not particularly limited. Examples of the material of the working electrode and the counter electrode include gold (Au), carbon (C), platinum (Pt), and titanium (Ti). Examples of the mediator include ferricyanide compounds (for example, potassium ferricyanide), metal complexes (for example, ruthenium complex, osmium complex, and vanadium complex), and quinone compounds (for example, pyrroloquinoline quinone). The structure of the glucose sensor and the electrochemical measurement method using the glucose sensor are detailed in, for example, Practical Cases of Biological Electrochemistry—Practical Development of Biosensor and Biobattery (published in March 2007, CMC Publishing CO., LTD.).

The enzyme of the present invention can be provided in a form of an enzyme preparation. The enzyme preparation may contain, in addition to an active ingredient (the present enzyme), excipient, buffer agents, suspension agents, stabilizer, preservatives, antiseptics, physiologic saline, and the like. Examples of the excipient may include starch, dextrin, maltose, trehalose, D-glucose, lactose, sorbitol, D-mannitol, sucrose, glycerol, and the like. Examples of the buffer agent may include phosphate, citrate, acetate, and the like. Examples of the stabilizer may include propylene glycol, and ascorbic acid, and the like. Examples of the preservative may include phenol, benzalkonium chloride, benzyl alcohol, chlorobutanol, methyl paraben, and the like. Examples of the antiseptic may include ethanol, benzalkonium chloride, parahydroxybenzoate, chlorobutanol, and the like.

EXAMPLES

1. Screening from Microorganism

Using the culture solutions obtained by culturing 13,000 strains containing preserved strains obtained from public institutions and strains obtained from nature as samples, those satisfying the following conditions, more specifically, having high glucose dehydrogenase activity, unreactivity to maltose, low reactivity to xylose, and no glucose oxidase activity were screened by the following methods.

Method for Measuring Glucose Dehydrogenase Activity (Measurement Test Solution)

100 mmol/L PIPES cont. 0.1% (w/v) Triton X-100 pH 7.0: 24 mL 3 mmol/L 1-Methoxy PMS (Phenazine methanesulfate): 2 mL 6.6 mmol/L NTB (Nitrotetrazorium blue): 1 mL 1 mol/L glucose: 3 mL (Measurement Procedure)

20 µL portions of the sample were dispensed into a 96-well plate, 200 µL portions of the measurement test solution were added to each well, and after 60 minutes at 37° C., the absorbance at 570 nm was measured with a plate reader. Of these measurement test solutions, glucose was changed to maltose or xylose and the same measurement was carried out, thereby also confirming reactivity to maltose and xylose.

Method for Measuring Glucose Oxidase Activity (Measurement Test Solution)

100 mmol/L PIPES cont. 0.1% (w/v) Triton X-100 pH 7.0: 23 mL 5 g/dL phenol reagent: 0.5 mL 25 u/mL PO "Amano"3 (Amano Enzyme Inc.) solution: 3 mL 0.5 g/dL 4-aminoantipyrine test solution: 0.5 mL 1 mol/L glucose: 3 mL (Measurement Procedure)

20 µL portions of the sample were dispensed into a 96-well plate, 200 µL portions of the measurement test solution were added to each well, and after 60 minutes at 37° C., the absorbance at 500 nm was measured with a plate reader.

As a result of the study, glucose dehydrogenase produced by the *Aspergillus iizukae* No. 5453 strain was found to have no reactivity to maltose, low reactivity to xylose, and be different from glucose oxidase. As to the *Aspergillus iizukae* No. 5453 strain, reactivity to maltose and xylose and glucose oxidase (GO) activity are listed in the following table. Reactivity to maltose and xylose is represented as the relative value when the reactivity to glucose is 100% (the measurement value using maltose (or xylose) as substrate/measurement value using glucose as substrate×100). Additionally, glucose oxidase (GO) was represented as the relative value to glucose dehydrogenase (measurement value of glucose oxidase (GO) activity/measurement value of glucose dehydrogenase activity×100). For comparison, the results of glucose oxidase (*Aspergillus niger*-derived), PQQ-dependent glucose dehydrogenase (*Acinetobacter calcoaceticus*-derived), and FAD-dependent glucose dehydrogenase (*Aspergillus oryzae*-derived) are also listed.

TABLE 1

|  | Maltose | Xylose | GO |
|---|---|---|---|
| Glucose oxydase | 1.7 | 3.4 | 543.7 |
| PQQ-dependent glucose dehydrogenase | 99.6 | 39.2 | 0.4 |
| FAD-dependent glucose dehydrogenase | 5.8 | 31.2 | 0 |
| *Aspergillus iizukae* No. 5453 | 5.1 | 9.3 | 13.0 |

It is indicated that the glucose dehydrogenase produced by the *Aspergillus iizukae* No. 5453 strain has advantageously lower reactivity to maltose and xylose than existing PQQ-dependent glucose dehydrogenase and FAD-dependent glucose dehydrogenase. The *Aspergillus iizukae* No. 5453 strain is the same strain as the *Aspergillus iizukae* Sugiyama NBRC 8869 deposited in NITE Biological Resource Center (NBRC) (2-5-8 Kazusakamatari, Kisarazu, Chiba, 292-0818).

2. Preparation of Purified Enzyme

As to the glucose dehydrogenase produced by the *Aspergillus iizukae* No. 5453 strain found by the above-mentioned study, in order to obtain its purified enzyme, the *Aspergillus iizukae* No. 5453 strain was cultured on the following culture medium at 30° C. for five days. The cell body were removed from the culture solution thus obtained, and used as the crude enzyme liquid.

(Culture medium)

Glucose: 15.0% (w/v)

Yeast extract: 3.0% (w/v)

Soybean peptone: 6.0% (w/v)

$KH_2PO_4$: 0.3% (w/v)

$K_2HPO_4$: 0.2% (w/v)

Hydroquinone (pH 6.0): 4 mM

The crude enzyme liquid was purified (salting out, hydrophobic bond chromatography, ion exchange chromatography, gel filtration chromatography), thus obtaining a purified enzyme. The purified enzyme was analyzed by gel filtration (Superdex 200 manufactured by GE Healthcare) and SDS-PAGE. The result of SDS-PAGE is given in FIG. 1. The fraction having the highest glucose dehydrogenase activity (No. 34) was used in the following experiments.

3. Confirmation of Substrate Specificity of Purified Enzyme

The substrate specificity of the purified enzyme obtained in the above-mentioned section 2 was examined.

(Activity Measurement Method)

FAD-GDH catalyzes the reaction of forming D-glucono-δ-lactone through oxidation of hydroxyl groups of glucose in the presence of an electron acceptor. The activity of FAD-GDH was measured by the following reaction system.

[Math. 1]

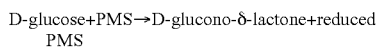

$$\text{D-glucose} + \text{PMS} \rightarrow \text{D-glucono-}\delta\text{-lactone} + \text{reduced PMS} \quad (1)$$

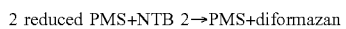

$$2 \text{ reduced PMS} + \text{NTB } 2 \rightarrow \text{PMS} + \text{diformazan} \quad (2)$$

The PMS in the formulae represents phenazine methanesulfate, and NTB represents nitrotetrazorium blue. In the reaction (1), reduced PMS is formed along with oxidation of glucose, and in the reaction (2), diformazan is formed through reduction of NTB by reduce PMS; the diformazan thus formed is measured at a wavelength of 570 nm.

The enzyme activity is calculated by the following calculation formula:

$$\text{Enzyme activity} \atop (U/mL) = \frac{\Delta OD/\min(\Delta OD_{test} - \Delta OD_{blank}) \times Vt \times df}{20.1 \times 1.0 \times Vs} \quad [\text{Math. 2}]$$

In the formula, Vt represents the total amount of the liquid, Vs represents the sample amount, 20.1 represents the absorbance coefficient (cm²/0.5 μmol) of diformazan per 0.5 μmol, 1.0 represents the optical path length (cm), and df represents the dilution rate.

2.4 mL of a 100 mmol/L PIPES-NaOH buffer at pH 7.0 containing 0.1% (w/v) triton X-100, 0.3 mL of 1 mol/L D-glucose solution, 0.2 mL of 3 mmol/L PMS solution, and 0.1 mL of 6.6 mmol/L NTB solution were mixed, and incubated at 37° C. for 5 minutes, then 0.1 mL of the enzyme liquid was added, thus initiating the reaction. Along with the progress of the enzyme reaction, diformazan having an absorption at 570 nm is formed. The increase of the absorbance at 570 nm per one minute was measured, thus measuring the FAD-GDH activity. The result is given in the following table. Additionally, the same measurement was carried out except that glucose was replaced with maltose or xylose, thereby confirming reactivity to maltose and xylose. For comparison, the result of the glucose dehydrogenase (GDH"Amano"8 Amano Enzyme Inc.) produced by *Aspergillus oryzae* is also given.

TABLE 2

|  | Relative activity | |
| --- | --- | --- |
|  | *Aspergillus iizukae* No. 5453 | *Aspergillus oryzae* |
| Glucose | 100 | 100 |
| Maltose | 0 | 0 |
| Xylose | 6.8 | 24 |

It was found that the glucose dehydrogenase produced by *Aspergillus iizukae* No. 5453 strain has lower reactivity to xylose than the glucose dehydrogenase produced by *Aspergillus oryzae*, and does not react to maltose, so that it has properties suitable for blood glucose measurement.

4. Confirmation of pH Stability of Purified Enzyme

The pH stability of the purified enzyme obtained in the above-mentioned 2 was examined. The enzyme liquid was prepared to 1 U/mL with buffer solutions at different pHs, and then warmed at 37° C. for 1 hour. Thereafter, the liquid was diluted with the buffer solution used for measurement, and the residual activity was measured by the same method as the above-mentioned 3.

Figure 2:
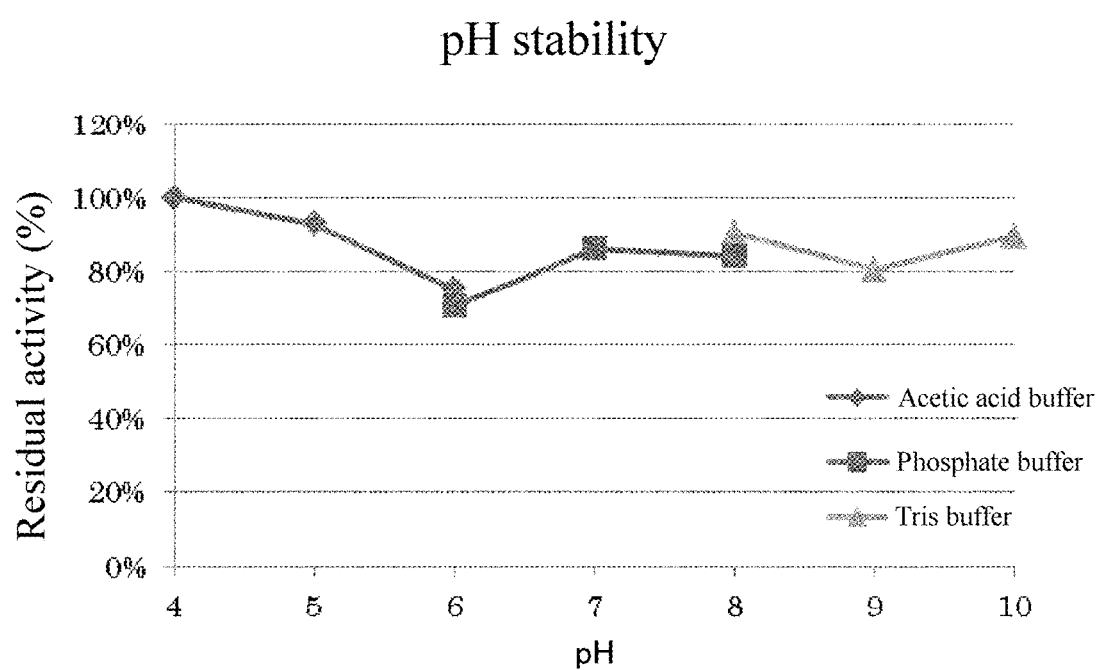
FIG. 2 The pH stability of purified enzyme. After predetermined treatment (37° C., 1 hour), its residual activity was measured.

The measurement result is given in FIG. 2. It exhibited high stability in the range of pH 4 to pH 10 (residual activity was 70% or more). As to a blood glucose measuring sensor, it is known that the pH during reaction must be adjusted according to the type of the mediator (electron acceptor) used concurrently with the enzyme. The present enzyme exhibited high stability over a wide pH range. This property allows the use of various mediators. More specifically, it was found that the present enzyme has properties suitable for blood glucose measurement.

5. Determination of N-Terminal Amino Acid and Internal Amino Acid Sequence

The band obtained by isolating the fraction No. 34, which is the active peak of the target enzyme, with SDS-PAGE was blotted on a PVDF membrane according to a common procedure, and then subjected to N-terminal amino acid analysis; the sequence information of "SSSYDYIVIGGGTSGLTVAN (SEQ ID NO: 3)" was obtained with a protein of about 60 KDa (FIG. 1, indicated with an arrow). Using this sequence as the inquiry sequence, BLAST analysis provided by NCBI was carried out; there was a high possibility that it is glucose dehydrogenase. The result of BLAST analysis is given in FIG. 3.

In the next place, in order to obtain the full length sequence of the present protein, the analysis of the internal amino acid was carried out. Firstly, trypsinization (digestion in the gel) was carried out by the following method, and the peptide fragment thus obtained was isolated by high performance liquid chromatograph (HPLC). Thereafter, amino acid analysis was carried out using the protein sequencer PPSQ-33A (Shimadzu Corporation).

(Trypsinization)
(i) The gel sample after electrophoresis is cut into an appropriate size.
(ii) The sample is subjected to reducing alkylation treatment using 2-mercaptoethanol and 4-vinylpyridine.
(iii) The sample is digested using Sequencing Grade Modified Trypsin manufactured by Promega Corporation in a buffer solution (0.1 mol/L ammonium hydrogencarbonate), and then the peptide fragment is extracted from the gel.

(HPLC Isolation Conditions)
High performance liquid chromatograph (HPLC): LC-20A system (Shimadzu Corporation)
Column: Cadenza CD-C18 (2.0 mm I.D.×150 mm) (Imtakt Corporation)
Column temperature: 50° C.
Detection wavelength: 214 mm
Injection amount: 70 μL
Mobile phase flow rate: 0.2 mL/min
Mobile phase A: water/trifluoroacetic acid (1000/1)
Mobile phase B: acetonitrile/water/trifluoroacetic acid (800/200/1)

FIG. 4 depicts the amino acid sequence identified by the analysis of the peaks obtained by HPLC isolation (13 peaks were identified, and numbered in the order from the short retention time to the long one).

6. Determination of Gene Sequence

On the basis of result of the N-terminal amino acid analysis obtained in the above-mentioned 5 and the result of the amino acid analysis of peak No. 5, the following primers were designed.

```
Primer GDH5453-F:
                                       (SEQ ID NO: 4)
TAYGAYTAYATHGTNATHGGNGGNGGNACNWSNGG Primer GDH5453-5-1-R:
                                       (SEQ ID NO: 5)
NSWNGCDATRTGNACRTTNCC
```

Using the genome DNA of the *Aspergillus iizukae* No. 5453 strain as the template, PCR was carried out using the designed primer and PrimeSTAR (registered trademark) Max DNA Polymerase (Takara Bio Inc.), thus obtaining an amplified DNA fragment. The PCR conditions were as follows.

(Reaction Liquid)
PrimeSTAR Max Premix (2×) 25 μL
GDH5453-F 15 pmol
GDH5453-5-1-R 15 pmol
Genome DNA (¹⁄₁₀₀₀ dilution) 1 μL
Adjusted to 50 μL with sterilized distilled water (Cycle Conditions)

35 cycles under conditions composed of 98° C. for 10 seconds, 55° C. for 15 seconds, and 72° C. for 2 minutes The DNA fragment thus obtained was subcloned using Mighty Cloning Reagent Set (Blunt End) (Takara Bio Inc.), and the base sequence of the DNA fragment was confirmed according to a common procedure.

On the basis of the base sequence (SEQ ID NO: 6) thus obtained, the following primer was designed.

```
Primer FS51R07F:
                                    (SEQ ID NO: 7)
AACCGTCTGTCTGAAGACCC Primer FS51R07R:
                                    (SEQ ID NO: 8)
TACTTCCTTTTGCTCG
```

Figure 5:
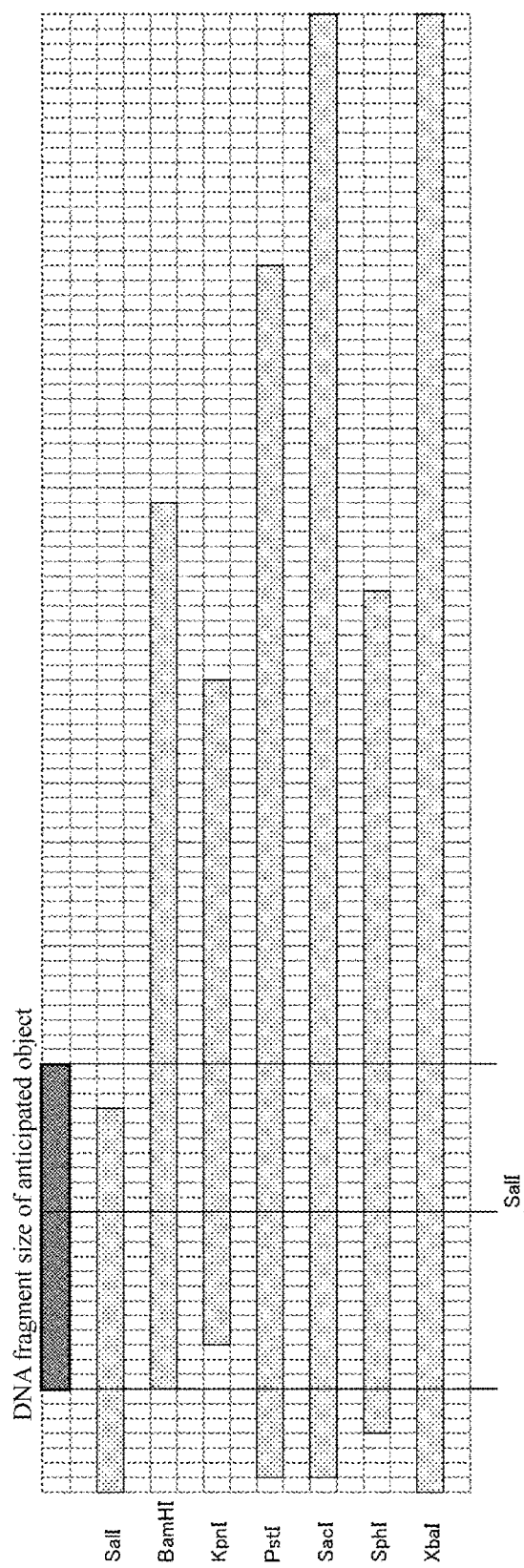
FIG. 5 The restriction enzyme map around the target gene (glucose dehydrogenase gene).

Using the above-mentioned DNA fragment as the template, PCR was carried out using the designed primer and PCR DIG Probe Synthesis Kit (Roche Diagnostics K.K.), thus obtaining a DNA probe labeled with digoxigenin. Southern hybridization was carried out using the probe. The chromosomal DNA completely digested with the restriction enzymes BamHI, KpnI, PstI, SacI, SphI, and XbaI, and that completely digested with a combination of these restriction enzymes and the restriction enzyme SalI were separated by 0.8% agarose electrophoresis. Subsequently, the object was transferred to zeta-probe membrane (Bio-Rad Laboratories Inc.), thus obtaining a membrane for southern hybridization. Southern hybridization was carried out using DIG Easy Hyb. (Roche Diagnostics K.K.) according to a common procedure. Detection was carried out using the digoxigenin antibody labeled with alkaline phosphatase, and the restriction enzyme map (FIG. 5) around the target gene was prepared from the detection result.

From the restriction enzyme map around the target DNA, it was indicated that the target gene was contained in the fragment of about 5.7 Kbp which had been completely digested with the restriction enzyme SphI, so that the chromosomal DNA completely digested with the restriction enzyme SphI was subjected to 0.8% agarose electrophoresis, and then the fragment around about 5.7 Kbp was collected from the agarose, and inserted into the restriction enzyme SphI site of the pUC18 (Takara Bio Inc.) plasmid. One thousand strains of the *Escherichia coli* (*E. coli*) JM109 (Takara Bio Inc.) transformed by the recombinant plasmid were prepared.

The colonies of the transformant thus obtained were transferred to a nylon membrane (Roche Diagnostics K.K.), and colony hybridization was carried out using DIG Easy Hyb. (Roche Diagnostics K.K.) according to a common procedure; several strains of positive clone were obtained. Plasmids were collected from the clone, and the base sequence was determined according to a common procedure. The amino acid sequence (SEQ ID NO: 1) anticipated from this base sequence (SEQ ID NO: 2) contained the N-terminal and internal amino acid sequence of the purified enzyme determined in the above-mentioned 5. From this finding, it was confirmed that the recombinant plasmid thus obtained contains the gene coding glucose dehydrogenase.

7. Preparation of Recombinant Enzyme and Evaluation of Properties

An expression cassette including the gene sequence of the glucose dehydrogenase produced by the *Aspergillus iizukae* No. 5453 strain placed between the Taka-amylase-modified CS3 promoter and terminator genes of *Aspergillus oryzae*-derived FAD-dependent glucose dehydrogenase, and an expression plasmid pUCPGDH5453 including the *Aspergillus oryzae*-derived orotidine 5'-phosphoric acid decarboxylase gene (pyrG gene) inserted into pUC19 were constructed. Using the constructed expression plasmid, the pyrG gene-defect strain of *Aspergillus oryzae* RIB40 was transformed by the protoplast-PEG method. A transformant was obtained using uridine auxotrophy. The transformant was liquid-cultured using soluble starch as C source under Taka-amylase induction conditions, and the culture solution containing the recombinant enzyme was collected. The collected culture solution was subjected to various kinds of purification (salting out, hydrophobic bond chromatography, and ion exchange chromatography), thus obtaining a purified enzyme. Various properties of the purified enzyme were evaluated.

(1) pH Stability

Figure 6:
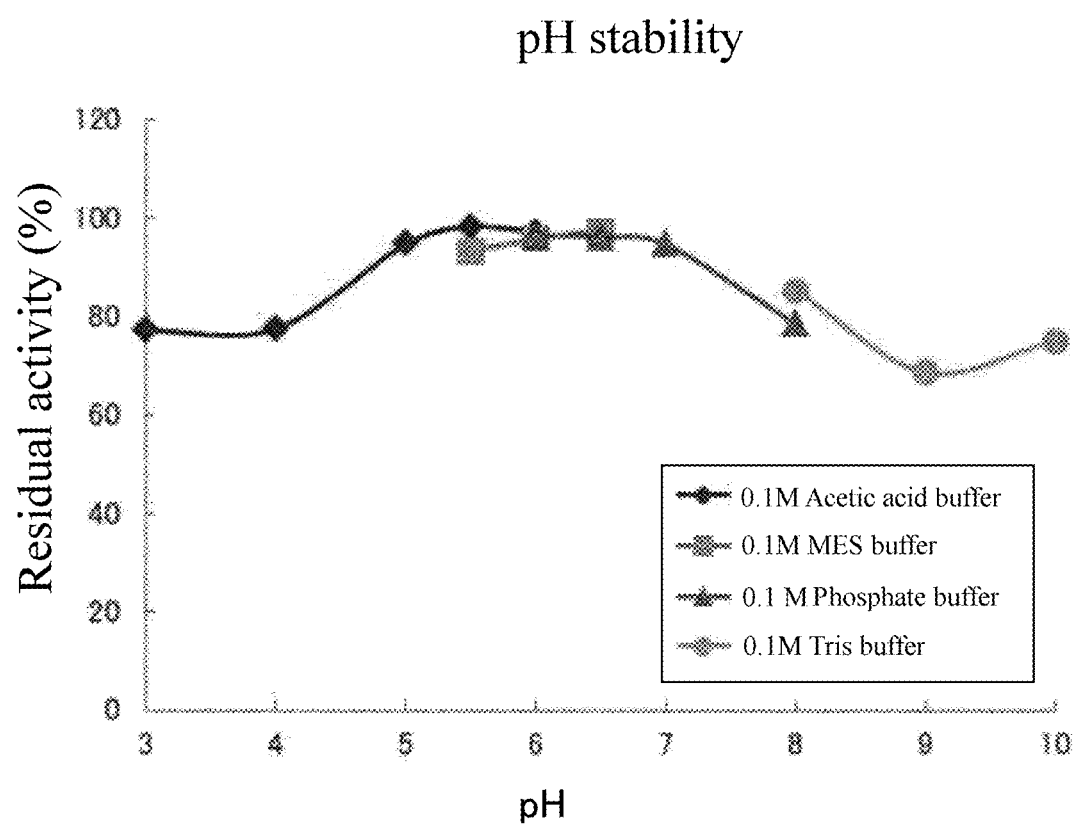
FIG. 6 The pH stability of the recombinant enzyme. After predetermined treatment (37° C., 1 hour), its residual activity was measured.

An enzyme liquid at 2 U/mL was prepared with buffer solution at various pHs, and treated under warming at 37° C. for 1 hour. Thereafter, the liquid was diluted with a buffer solution used for measurement, and the residual activity was measured. The measurement result is shown in FIG. 6. The purified enzyme exhibited high stability after treatment for 1 hour at 37° C. and pH 3 to 10 (residual activity was 70% or more).

(2) Optimum pH

Figure 7:
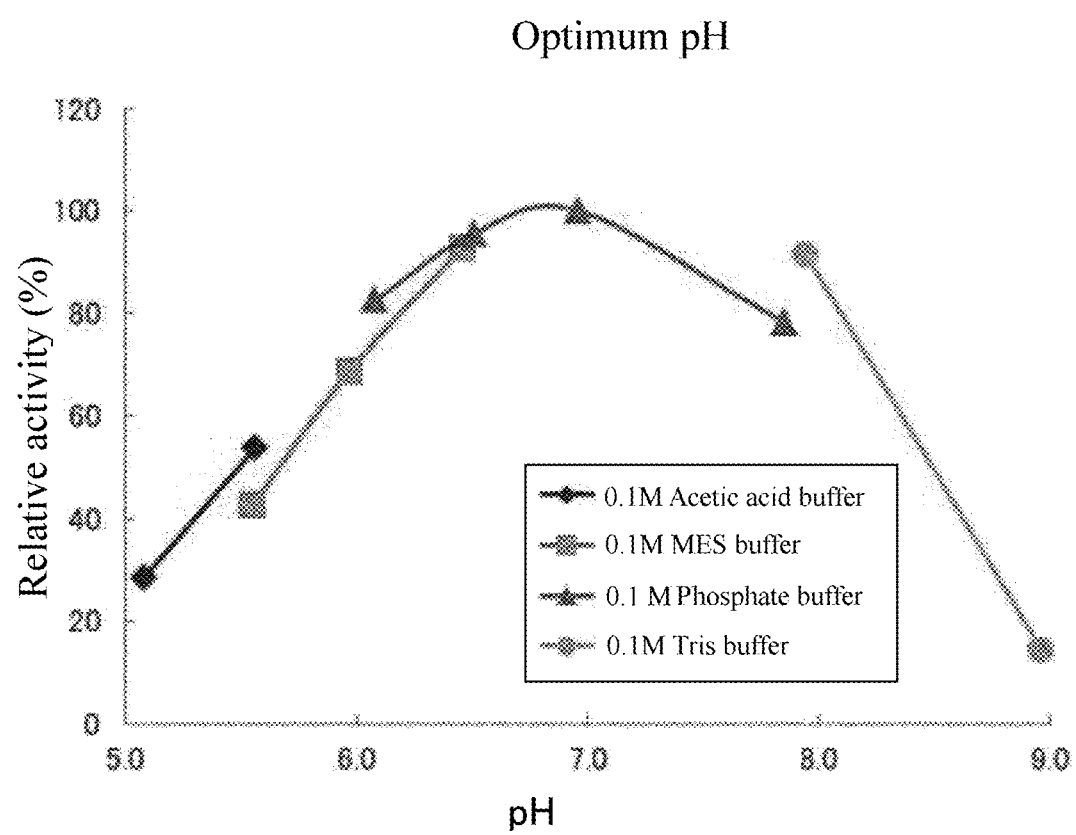
FIG. 7 The optimum pH of the recombinant enzyme. Its activity was measured with a buffer solution at various pHs.

The buffer solution used was replaced with other buffer solutions at various pHs, and the activity was measured to confirm the optimum pH. The measurement result is given in FIG. 7. The optimum pH of the enzyme reaction was 7.0.

(3) Optimum Temperature

Figure 8:
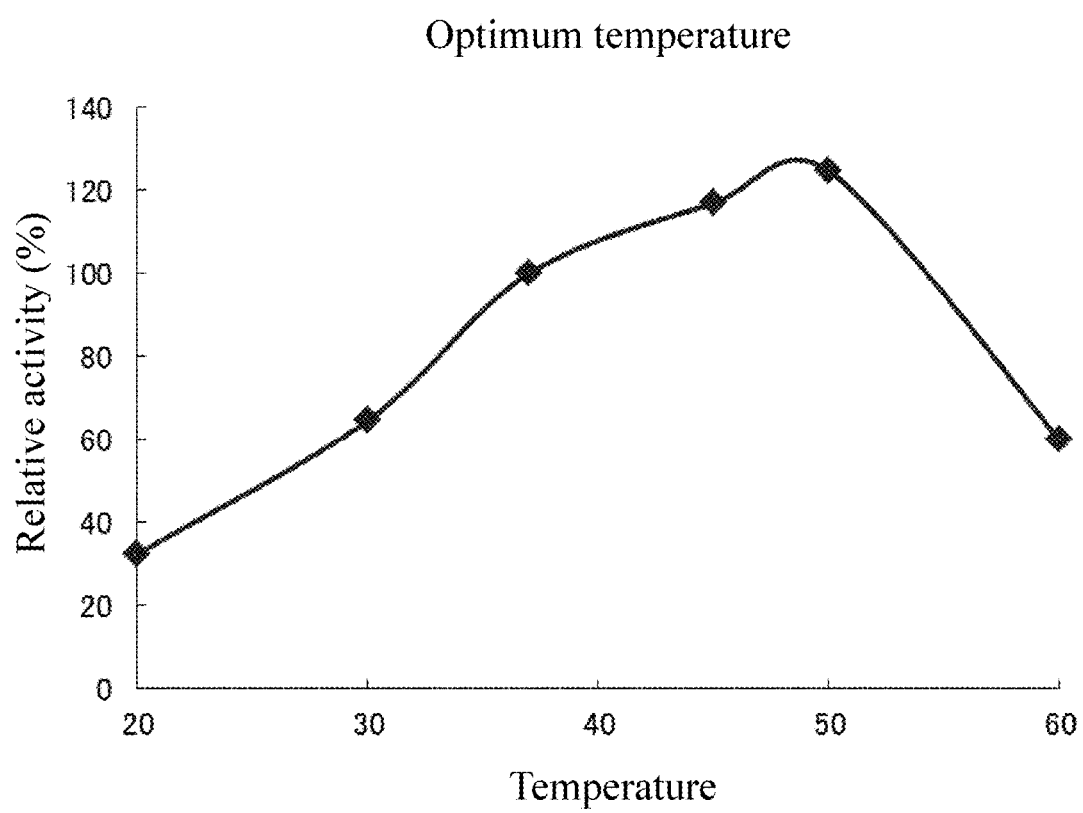
FIG. 8 The optimum temperature of the recombinant enzyme. Its activity was measured at different temperatures.

The activity was measured at different temperatures to confirm the optimum temperature. The measurement result is given in FIG. 8. The optimum temperature of the enzyme reaction was 50° C.

(4) Thermostability

Figure 9:
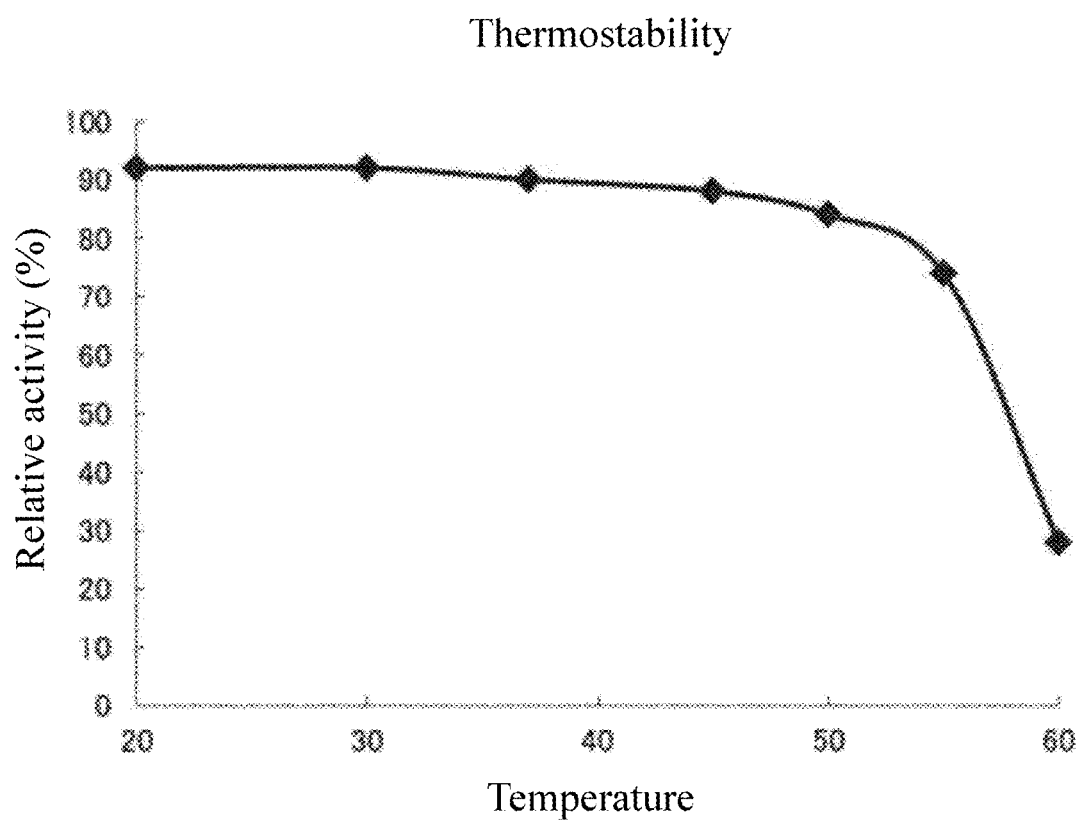
FIG. 9 The thermostability of the recombinant enzyme. After predetermined treatment (different temperatures, 1 hour), its residual activity was measured.

An enzyme liquid of 2 U/mL was prepared with 50 mM acetic acid-NaOH (pH 5.0), then warmed for one hour at each temperature. After the treatment, the liquid was immediately stored in ice, and the residual activity was measured. The measurement result is given in FIG. 9. High stability was exhibited when the temperature of the warming treatment was 50° C. or lower (the residual activity was 80% or more).

INDUSTRIAL APPLICABILITY

The glucose dehydrogenase of the present invention has low reactivity to xylose, and has marked pH stability. The glucose dehydrogenase of the present invention is particularly suitable for the application to a glucose sensor, and its practicality is high.

The present invention is not limited to the above-mentioned embodiments and examples of the invention. Various modifications easily conceived by those skilled in the art are included in the present invention without departing from the scope of the invention. The entire contents of all of the literatures, unexamined patent publications, and patent publications cited in the present description are incorporated herein by reference.

[Sequence Listing]

The invention claimed is:

1. A recombinant DNA comprising a DNA selected from the group consisting of the following (A) and (B):
   (A) a DNA comprising the nucleotide sequence set forth in SEQ ID NO: 2; and
   (B) a DNA comprising a nucleotide sequence that has 90% or more sequence identity to the nucleotide sequence set forth in SEQ ID NO: 2, and encoding a protein having glucose dehydrogenase activity.

2. A microorganism comprising the recombinant DNA according to claim 1.

3. A method for producing glucose dehydrogenase comprising the following steps (1) and (2), or the following steps (i) and (ii):
   (1) culturing an *Aspergillus* iizukae NBRC 8869 strain in a culture solution, wherein the *Aspergillus* iizukae NBRC 8869 strain produces glucose dehydrogenase comprising the amino acid sequence of SEQ ID NO: 1; and
   (2) collecting the glucose dehydrogenase from the culture solution and/or the *Aspergillus* iizukae NBRC 8869 fungal cells after culturing;
   (i) culturing a microorganism to produce a protein having glucose dehydrogenase activity, wherein the microorganism is transformed with a plasmid comprising a polynucleotide with a nucleotide sequence encoding the protein having glucose dehydrogenase activity, wherein the nucleotide sequence encoding the protein having glucose dehydrogenase activity is selected from the group consisting of the following (a) to (d):
   (a) a nucleotide sequence encoding the amino acid sequence set forth in SEQ ID NO: 1;
   (b) a nucleotide sequence encoding an the amino acid sequence with 90% or more sequence identity to the amino acid sequence set forth in SEQ ID NO: 1 and having glucose dehydrogenase activity;
   (c) the nucleotide sequence set forth in SEQ ID NO: 2; and
   (d) a nucleotide sequence with 90% or more sequence identity to the nucleotide sequence set forth in SEQ ID NO: 2 and encoding a protein having glucose dehydrogenase activity; and
   (ii) collecting the protein having glucose dehydrogenase activity produced in step (i).

* * * * *